United States Patent
Sathe et al.

(10) Patent No.: US 6,277,977 B1
(45) Date of Patent: Aug. 21, 2001

(54) CDNA CLONE HAPOI67 THAT ENCODES A HUMAN 7-TRANSMEMBRANE RECEPTOR

(75) Inventors: Ganesh Madhusudan Sathe, King of Prussia, PA (US); Joyce Yue Mao, Westmont, NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 08/956,322

(22) Filed: Oct. 23, 1997

Related U.S. Application Data

(60) Provisional application No. 60/049,329, filed on Jun. 11, 1997.

(51) Int. Cl.$^7$ .................................................. C12N 15/12
(52) U.S. Cl. ........................................ 536/23.5; 536/23.1
(58) Field of Search ................................. 536/23.1, 23.5; 435/325, 320.1, 96.1

(56) References Cited

PUBLICATIONS

Rudinger, In "Peptide Hormones" (ed. J. A. Parsons) University Park Press, Baltimore, pp. 1–7, 1976.*

Hillier et al., GenBank Accession #H70763, cDNA Clone 213982 (submitted 1995).

McKnight, Andrew J. et al., "Molecular Cloning of F4/80, a Murine Macrophage–restricted Cell Surface Glycoprotein with Homology to the G–protein–linked Transmembrane 7 Hormone Receptor Family", J. Biol. Chem. 271: 486–489 (1996).

Baud, V., et al, "EMR1, an Unusual Member in the Family of Hormone Receptors with Seven Transmembrane Segments", Genomics 26, 334–344 (1995).

* cited by examiner

Primary Examiner—Christina Y. Chan
Assistant Examiner—Robert C. Hayes
(74) Attorney, Agent, or Firm—Elizabeth J. Hecht; Ratner & Prestia; William T. King

(57) ABSTRACT

HAPOI67 polypeptides and polynucleotides and methods for producing such polypeptides by recombinant techniques are disclosed. Also disclosed are methods for utilizing HAPOI67 polypeptides and polynucleotides in the design of protocols for the treatment of infections such as bacterial, fungal, protozoan and viral infections, particularly infections caused by HIV-1 or HIV-2; pain; cancers; anorexia; bulimia asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others and diagnostic assays for such conditions.

5 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2329 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
AAGCAGTTTG CTTTTCTGAT AGCAATTTCA TGAGTCAGCT GACCTAAGAT ACATACTTCA      60

ATTCTCATGG GATTTCTTGA GCTAGGAAAG GTGGTTGGCT TACGGCACAG TAGAGAGCTT     120

CCAGGGCTGG CTGGCGTGGG ATACCCGTAC CACAGAAATG CAGGGACCAT TGCTTCTTCC     180

AGGCCTCTGC TTTCTGCTGA GCCTCTTTGG AGCTGTGACT CAGAAAACCA AAACTTCCTG     240

TGCTAAGTGC CCCCCAAATG CTTCCTGTGT CAATAACACT CACTGCACCT GCAACCATGG     300

ATATACTTCT GGATCTGGGC AGAAACTATT CACATTCCCC TTGGAGACAT GTAACGACAT     360

TAATGAATGT ACACCACCCT ATAGTGTATA TTGTGGATTT AACGCTGTGT GTTACAATGT     420

CGAAGGAAGT TTCTACTGTC AATGTGTCCC AGGATATAGA CTGCATTCTG GGAATGAACA     480

ATTCAGTAAT TCCAATGAGA ACACCTGTCA GGACACCACC TCCTCAAAGA CAACCCAGGG     540

CAGGAAAGAG CTGCAAAAGA TTGTGGACAA ATTTGAGTCA CTTCTCACCA ATCAGACTTT     600

ATGGAGAACA GAAGGGAGAC AAGAAATCTC ATCCACAGCT ACCACTATTC TCCGGGATGT     660

GGAATCGAAA GTTCTAGAAA CTGCCTTGAA AGATCCAGAA CAAAAAGTCC TGAAAATCCA     720

AAACGATAGT GTAGCTATTG AAACTCAAGC GATTACAGAC AATTGCTCTG AAGAAAGAAA     780

GACATTCAAC TTGAACGTCC AAATGAACTC AATGGACATC CGTTGCAGTG ACATCATCCA     840

GGGAGACACA CAAGGTCCCA GTGCCATTGC CTTTATCTCA TATTCTTCTC TTGGAAACAT     900

CATAAATGCA ACTTTTTTTG AAGAGATGGA TAAGAAAGAT CAAGTGTATC TGAACTCTCA     960
```

-continued

```
GGTTGTGAGT GCTGCTATTG GACCCAAAAG GAACGTGTCT CTCTCCAAGT CTGTGACGCT    1020

GACTTTCCAG CACGTGAAGA TGACCCCCAG TACCAAAAAG GTCTTCTGTG TCTACTGGAA    1080

GAGCACAGGG CAGGGCAGCC AGTGGTCCAG GGATGGCTGC TTCCTGATAC ACGTGAACAA    1140

GAGTCACACC ATGTGTAATT GCAGTCACCT GTCCAGCTTC GCTGTCCTGA TGGCCCTGAC    1200

CAGCCAGGAG GAGGATCCCG TGCTGACTGT CATCACCTAC GTGGGCTGA GCGTCTCTCT    1260

GCTGTGCCTC CTCCTGGCGG CCCTCACTTT TCTCCTGTGT AAAGCCATCC AGAACACCAG    1320

CACCTCACTG CATCTGCAGC TCTCGCTCTG CCTCTTCCTG GCCCACCTCC TCTTCCTCGT    1380

GGGGATTGAT CGAACTGAAC CCAAGGTGCT GTGCTCCATC ATCGCCGGTG CTTTGCACTA    1440

TCTCTACCTG GCCGCCTTCA CCTGGATGCT GCTGGAGGGT GTGCACCTCT TCCTCACTGC    1500

ACGGAACCTG ACAGTGGTCA ACTACTCAAG CATCAATAGA CTCATGAAGT GGATCATGTT    1560

CCCAGTCGGC TATGGCGTTC CCGCTGTGAC TGTGGCCATT TCTGCAGCCT CCTGGCCTCA    1620

CCTTTATGGA ACTGCTGATC GATGCTGGCT CCACCTGGAC CAGGGATTCA TGTGGAGTTT    1680

CCTTGGCCCA GTCTGTGCCA TTTTCTCTGC GAATTTAGTA TTGTTTATCT TGGTCTTTTG    1740

GATTTTGAAA AGAAAACTTT CCTCCCTCAA TAGTGAAGTG TCAACCATCC AGAACACAAG    1800

GATGCTGGCT TTCAAAGCAA CAGCTCAGCT CTTCATCCTG GGCTGCACAT GGTGTCTGGG    1860

CTTGCTACAG GTGGGTCCAG CTGCCCAGGT CATGGCCTAC CTCTTCACCA TCATCAACAG    1920

CCTCCAAGGC TTCTTCATCT TCTTGGTCTA CTGCCTCCTC AGCCAGCAGG TCCAGAAACA    1980

ATATCAAAAG TGGTTTAGAG AGATCGTAAA ATCAAAATCT GAGTCTGAGA CATACACACT    2040

TTCCAGCAAG ATGGGTCCTG ACTCAAAACC CAGTGAGGGG GATGTTTTTC CAGGACAAGT    2100

GAAGAGAAAA TATTAAAACT AGAATATTCA ACTCCATATG GAAAATCATA TCCATGGATC    2160

TCTTTGGCAT TATGAAGAAT GAAGCTAAGG AAAAGGGAAT TCATTAAACA TATCATCCTT    2220

GGAGAGGAAG TAATCAACCT TTACTTCCCA AGCTGTTTGT TCTCCACAAT AGGCTCTCAA    2280

CAAATGTGTG GTAAATTGCA TTTCTCTTCA AAAAAAAAAA AAAAAAAA               2329
```

(2) INFORMATION FOR SEQ ID NO:2:

(i) SEQUENCE CHARACTERISTICS:
        (A) LENGTH: 652 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Gln Gly Pro Leu Leu Pro Gly Leu Cys Phe Leu Leu Ser Leu
 1               5                  10                  15

Phe Gly Ala Val Thr Gln Lys Thr Lys Thr Ser Cys Ala Lys Cys Pro
            20                  25                  30

Pro Asn Ala Ser Cys Val Asn Asn Thr His Cys Thr Cys Asn His Gly
                35                  40                  45

Tyr Thr Ser Gly Ser Gly Gln Lys Leu Phe Thr Phe Pro Leu Glu Thr
        50                  55                  60

Cys Asn Asp Ile Asn Glu Cys Thr Pro Pro Tyr Ser Val Tyr Cys Gly
65                  70                  75                  80

Phe Asn Ala Val Cys Tyr Asn Val Glu Gly Ser Phe Tyr Cys Gln Cys
                85                  90                  95

Val Pro Gly Tyr Arg Leu His Ser Gly Asn Glu Gln Phe Ser Asn Ser
```

```
                    100                 105                 110
Asn Glu Asn Thr Cys Gln Asp Thr Thr Ser Ser Lys Thr Thr Gln Gly
            115                 120                 125
Arg Lys Glu Leu Gln Lys Ile Val Asp Lys Phe Glu Ser Leu Leu Thr
            130                 135                 140
Asn Gln Thr Leu Trp Arg Thr Glu Gly Arg Gln Glu Ile Ser Ser Thr
145                 150                 155                 160
Ala Thr Thr Ile Leu Arg Asp Val Glu Ser Lys Val Leu Glu Thr Ala
                165                 170                 175
Leu Lys Asp Pro Glu Gln Lys Val Leu Lys Ile Gln Asn Asp Ser Val
            180                 185                 190
Ala Ile Glu Thr Gln Ala Ile Thr Asp Asn Cys Ser Glu Glu Arg Lys
        195                 200                 205
Thr Phe Asn Leu Asn Val Gln Met Asn Ser Met Asp Ile Arg Cys Ser
        210                 215                 220
Asp Ile Ile Gln Gly Asp Thr Gln Gly Pro Ser Ala Ile Ala Phe Ile
225                 230                 235                 240
Ser Tyr Ser Ser Leu Gly Asn Ile Ile Asn Ala Thr Phe Phe Glu Glu
                245                 250                 255
Met Asp Lys Lys Asp Gln Val Tyr Leu Asn Ser Gln Val Val Ser Ala
            260                 265                 270
Ala Ile Gly Pro Lys Arg Asn Val Ser Leu Ser Lys Ser Val Thr Leu
            275                 280                 285
Thr Phe Gln His Val Lys Met Thr Pro Ser Thr Lys Lys Val Phe Cys
        290                 295                 300
Val Tyr Trp Lys Ser Thr Gly Gln Gly Ser Gln Trp Ser Arg Asp Gly
305                 310                 315                 320
Cys Phe Leu Ile His Val Asn Lys Ser His Thr Met Cys Asn Cys Ser
                325                 330                 335
His Leu Ser Ser Phe Ala Val Leu Met Ala Leu Thr Ser Gln Glu Glu
            340                 345                 350
Asp Pro Val Leu Thr Val Ile Thr Tyr Val Gly Leu Ser Val Ser Leu
            355                 360                 365
Leu Cys Leu Leu Leu Ala Ala Leu Thr Phe Leu Leu Cys Lys Ala Ile
        370                 375                 380
Gln Asn Thr Ser Thr Ser Leu His Leu Gln Leu Ser Leu Cys Leu Phe
385                 390                 395                 400
Leu Ala His Leu Leu Phe Leu Val Gly Ile Asp Arg Thr Glu Pro Lys
                405                 410                 415
Val Leu Cys Ser Ile Ile Ala Gly Ala Leu His Tyr Leu Tyr Leu Ala
            420                 425                 430
Ala Phe Thr Trp Met Leu Leu Glu Gly Val His Leu Phe Leu Thr Ala
            435                 440                 445
Arg Asn Leu Thr Val Val Asn Tyr Ser Ser Ile Asn Arg Leu Met Lys
        450                 455                 460
Trp Ile Met Phe Pro Val Gly Tyr Gly Val Pro Ala Val Thr Val Ala
465                 470                 475                 480
Ile Ser Ala Ala Ser Trp Pro His Leu Tyr Gly Thr Ala Asp Arg Cys
                485                 490                 495
Trp Leu His Leu Asp Gln Gly Phe Met Trp Ser Phe Leu Gly Pro Val
            500                 505                 510
Cys Ala Ile Phe Ser Ala Asn Leu Val Leu Phe Ile Leu Val Phe Trp
        515                 520                 525
```

```
Ile Leu Lys Arg Lys Leu Ser Ser Leu Asn Ser Glu Val Ser Thr Ile
    530                 535                 540

Gln Asn Thr Arg Met Leu Ala Phe Lys Ala Thr Ala Gln Leu Phe Ile
545                 550                 555                 560

Leu Gly Cys Thr Trp Cys Leu Gly Leu Leu Gln Val Gly Pro Ala Ala
                565                 570                 575

Gln Val Met Ala Tyr Leu Phe Thr Ile Ile Asn Ser Leu Gln Gly Phe
            580                 585                 590

Phe Ile Phe Leu Val Tyr Cys Leu Leu Ser Gln Val Gln Lys Gln
        595                 600                 605

Tyr Gln Lys Trp Phe Arg Glu Ile Val Lys Ser Lys Ser Glu Ser Glu
    610                 615                 620

Thr Tyr Thr Leu Ser Ser Lys Met Gly Pro Asp Ser Lys Pro Ser Glu
625                 630                 635                 640

Gly Asp Val Phe Pro Gly Gln Val Lys Arg Lys Tyr
                645                 650
```

(2) INFORMATION FOR SEQ ID NO:3:

(i) SEQUENCE CHARACTERISTICS:
        (A) LENGTH: 2207 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGCACGAGCT GGCGTGGGAT ACCCGTACCA CAGAAATGCA GGGACCATTG CTTCTTCCAG      60

GCCTCTGCTT TCTGCTGAGC CTCTTTGGAG CTGTGACTCA GAAAACCAAA ACTTCCTGTG     120

CTAAGTGCCC CCCAAATGCT TCCTGTGTCA ATAACACTCA CTGCACCTGC AACCATGGAT     180

ATACTTCTGG ATCTGGGCAG AAACTATTCA CATTCCCCTT GGAGACATGT AACGACATTA     240

ATGAATGTAC ACCACCCTAT AGTGTATATT GTGGATTTAA CGCTGTGTGT TACAATGTCG     300

AAGGAAGTTT CTACTGTCAA TGTGTCCCAG GATATAGACT GCATTCTGGG AATGAACAAT     360

TCAGTAATTC CAATGAGAAC ACCTGTCAGG ACACCACCTC CTCAAAGACA ACCCAGGGCA     420

GGAAAGAGCT GCAAAAGATT GTGGACAAAT TTGAGTCACT TCTCACCAAT CAGACTTTAT     480

GGAGAACAGA AGGGAGACAA GAAATCTCAT CCACAGCTAC CACTATTCTC CGGGATGTGG     540

AATCGAAAGT TCTAGAAACT GCCTTGAAAG ATCCAGAACA AAAGTCCTG AAAATCCAAA     600

ACGATAGTGT AGCTATTGAA ACTCAAGCGA TTACAGACAA TTGCTCTGAA GAAAGAAAGA     660

CATTCAACTT GAACGTCCAA ATGAACTCAA TGGACATCCG TTGCAGTGAC ATCATCCAGG     720

GAGACACACA AGGTCCCAGT GCCATTGCCT TTATCTCATA TTCTTCTCTT GGAAACATCA     780

TAAATGCAAC TTTTTTTGAA GAGATGGATA AGAAAGATCA AGTGTATCTG AACTCTCAGG     840

TTGTGAGTGC TGCTATTGGA CCCAAAAGGA ACGTGTCTCT CTCCAAGTCT GTGACGCTGA     900

CTTTCCAGCA CGTGAAGATG ACCCCCAGTA CCAAAAAGGT CTTCTGTGTC TACTGGAAGA     960

GCACAGGGCA GGGCAGCCAG TGGTCCAGGG ATGGCTGCTT CCTGATACAC GTGAACAAGA    1020

GTCACACCAT GTGTAATTGC AGTCACCTGT CCAGCTTCGC TGTCCTGATG GCCCTGACCA    1080

GCCAGGAGGA GGATCCCGTG CTGACTGTCA TCACCTACGT GGGGCTGAGC GTCTCTCTGC    1140

TGTGCCTCCT CCTGGCGGCC CTCACTTTTC TCCTGTGTAA AGCCATCCAG AACACCAGCA    1200

CCTCACTGCA TCTGCAGCTC TCGCTCTGCC TCTTCCTGGC CCACCTCCTC TTCCTCGTGG    1260
```

```
GGATTGATCG AACTGAACCC AAGGTGCTGT GCTCCATCAT CGCCGGTGCT TTGCACTATC  1320

TCTACCTGGC CGCCTTCACC TGGATGCTGC TGGAGGGTGT GCACCTCTTC CTCACTGCAC  1380

GGAACCTGAC AGTGGTCAAC TACTCAAGCA TCAATAGACT CATGAAGTGG ATCATGTTCC  1440

CAGTCGGCTA TGGCGTTCCC GCTGTGACTG TGGCCATTTC TGCAGCCTCC TGGCCTCACC  1500

TTTATGGAAC TGCTGATCGA TGCTGGCTCC ACCTGGACCA GGGATTCATG TGGAGTTTCC  1560

TTGGCCCAGT CTGTGCCATT TTCTCTGCGA ATTTAGTATT GTTTATCTTG GTCTTTTGGA  1620

TTTTGAAAAG AAAACTTTCC TCCCTCAATA GTGAAGTGTC AACCATCCAG AACACAAGGA  1680

TGCTGGCTTT CAAAGCAACA GCTCAGCTCT TCATCCTGGG CTGCACATGG TGTCTGGGCT  1740

TGCTACAGGT GGGTCCAGCT GCCCAGGTCA TGGCCTACCT CTTCACCATC ATCAACAGCC  1800

TCCAAGGCTT CTTCATCTTC TTGGTCTACT GCCTCCTCAG CCAGCAGGTC AGAAACAAT   1860

ATCAAAAGTG GTTTAGAGAG ATCGTAAAAT CAAAATCTGA GTCTGAGACA TACACACTTT  1920

CCAGCAAGAT GGGTCCTGAC TCAAAACCCA GTGAGGGGGA TGTTTTTCCA GGACAAGTGA  1980

AGAGAAAATA TTAAAACTAG AATATTCAAC TCCATATGGA AAATCATATC CATGGATCTC  2040

TTTGGCATTA TGAAGAATGA AGCTAAGGAA AAGGGAATTC ATTAAACATA TCATCCTTGG  2100

AGAGGAAGTA ATCAACCTTT ACTTCCCAAG CTGTTTGTTC TCCACAATAG GCTCTCAACA  2160

AATGTGTGGT AAATTGCATT TCTCTTCAAA AAAAAAAAAA AAAAAAA               2207
```

(2) INFORMATION FOR SEQ ID NO:4:

(i) SEQUENCE CHARACTERISTICS:
  (A) LENGTH: 521 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:4:

```
Leu Gln Lys Ile Val Asp Lys Phe Glu Ser Leu Leu Thr Asn Gln Thr
  1               5                  10                  15

Leu Trp Arg Thr Glu Gly Arg Gln Glu Ile Ser Ser Thr Ala Thr Thr
             20                  25                  30

Ile Leu Arg Asp Val Glu Ser Lys Val Leu Glu Thr Ala Leu Lys Asp
         35                  40                  45

Pro Glu Gln Lys Val Leu Lys Ile Gln Asn Asp Ser Val Ala Ile Glu
     50                  55                  60

Thr Gln Ala Ile Thr Asp Asn Cys Ser Glu Glu Arg Lys Thr Phe Asn
 65                  70                  75                  80

Leu Asn Val Gln Met Asn Ser Met Asp Ile Arg Cys Ser Asp Ile Ile
                 85                  90                  95

Gln Gly Asp Thr Gln Gly Pro Ser Ala Ile Ala Phe Ile Ser Tyr Ser
            100                 105                 110

Ser Leu Gly Asn Ile Ile Asn Ala Thr Phe Phe Glu Glu Met Asp Lys
        115                 120                 125

Lys Asp Gln Val Tyr Leu Asn Ser Gln Val Val Ser Ala Ala Ile Gly
    130                 135                 140

Pro Lys Arg Asn Val Ser Leu Ser Lys Ser Val Thr Leu Thr Phe Gln
145                 150                 155                 160

His Val Lys Met Thr Pro Ser Thr Lys Lys Val Phe Cys Val Tyr Trp
                165                 170                 175
```

-continued

```
Lys Ser Thr Gly Gln Gly Ser Gln Trp Ser Arg Asp Gly Cys Phe Leu
            180                 185                 190

Ile His Val Asn Lys Ser His Thr Met Cys Asn Cys Ser His Leu Ser
            195                 200                 205

Ser Phe Ala Val Leu Met Ala Leu Thr Ser Gln Glu Glu Asp Pro Val
            210                 215                 220

Leu Thr Val Ile Thr Tyr Val Gly Leu Ser Val Ser Leu Leu Cys Leu
225                 230                 235                 240

Leu Leu Ala Ala Leu Thr Phe Leu Leu Cys Lys Ala Ile Gln Asn Thr
                245                 250                 255

Ser Thr Ser Leu His Leu Gln Leu Ser Leu Cys Leu Phe Leu Ala His
            260                 265                 270

Leu Leu Phe Leu Val Gly Ile Asp Arg Thr Glu Pro Lys Val Leu Cys
            275                 280                 285

Ser Ile Ile Ala Gly Ala Leu His Tyr Leu Tyr Leu Ala Ala Phe Thr
            290                 295                 300

Trp Met Leu Leu Glu Gly Val His Leu Phe Leu Thr Ala Arg Asn Leu
305                 310                 315                 320

Thr Val Val Asn Tyr Ser Ser Ile Asn Arg Leu Met Lys Trp Ile Met
                325                 330                 335

Phe Pro Val Gly Tyr Gly Val Pro Ala Val Thr Val Ala Ile Ser Ala
            340                 345                 350

Ala Ser Trp Pro His Leu Tyr Gly Thr Ala Asp Arg Cys Trp Leu His
            355                 360                 365

Leu Asp Gln Gly Phe Met Trp Ser Phe Leu Gly Pro Val Cys Ala Ile
            370                 375                 380

Phe Ser Ala Asn Leu Val Leu Phe Ile Leu Val Phe Trp Ile Leu Lys
385                 390                 395                 400

Arg Lys Leu Ser Ser Leu Asn Ser Glu Val Ser Thr Ile Gln Asn Thr
                405                 410                 415

Arg Met Leu Ala Phe Lys Ala Thr Ala Gln Leu Phe Ile Leu Gly Cys
            420                 425                 430

Thr Trp Cys Leu Gly Leu Leu Gln Val Gly Pro Ala Ala Gln Val Met
            435                 440                 445

Ala Tyr Leu Phe Thr Ile Ile Asn Ser Leu Gln Gly Phe Phe Ile Phe
            450                 455                 460

Leu Val Tyr Cys Leu Leu Ser Gln Gln Val Gln Lys Gln Tyr Gln Lys
465                 470                 475                 480

Trp Phe Arg Glu Ile Val Lys Ser Lys Ser Glu Ser Glu Thr Tyr Thr
                485                 490                 495

Leu Ser Ser Lys Met Gly Pro Asp Ser Lys Pro Ser Glu Gly Asp Val
            500                 505                 510

Phe Pro Gly Gln Val Lys Arg Lys Tyr
            515                 520
```

CDNA CLONE HAPOI67 THAT ENCODES A HUMAN 7-TRANSMEMBRANE RECEPTOR

This application claims the benefit of U.S. Provisional Application Ser. No. 60/049,329, filed Jun. 11, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the G-protein coupled receptor family, hereinafter referred to as HAPOI67. The invention also relates to inhibiting or activating the action of such polynucleotides and polypeptides.

BACKGROUND OF THE INVENTION

It is well established that many medically significant biological processes are mediated by proteins participating in signal transduction pathways that involve G-proteins and/or second messengers, e.g., cAMP (Lefkowitz, Nature, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA, 1987, 84:46–50; Kobilka, B. K., et al., Science, 1987, 238:650–656; Bunzow, J. R., et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone binding is activation of the enzyme, adenylate cyclase, inside the cell. Enzyme activation by hormones is dependent on the presence of the nucleotide, GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, scrotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structures. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said sockets being surrounded by hydrophobic residues of the G-protein coupled receptors. The hydrophilic side of each G-protein coupled receptor transmembrane helix is postulated to face inward and form a polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317–331) Different G-protein α-subunits preferentially stimulate particular effectors to modulate various biological functions in a cell. Phosphorylation of cytoplasmic residues of G-protein coupled receptors has been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7 TM) receptors have been successfully introduced into the market.

This indicates that these receptors have an established, proven history as therapeutic targets. Clearly there is a need for identification and characterization of further receptors which can play a role in preventing, ameliorating or correcting dysfunctions or diseases, including, but not limited to, infections such as bacterial, fungal, protozoan and viral infections, particularly infections caused by HIV-1 or HIV-2; pain; cancers; anorexia; bulimia a; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

SUMMARY OF THE INVENTION

In one aspect, the invention relates to HAPOI67 polypeptides and recombinant materials and methods for their production. Another aspect of the invention relates to methods for using such HAPOI67 polypeptides and polynucleotides. Such uses include the treatment of infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. In still another aspect, the invention relates to methods to identify agonists and antagonists using the materials provided by the invention, and treating conditions associated with HAPOI67 imbalance with the identified compounds. Yet another aspect of the invention relates to diagnostic assays for detecting diseases associated with inappropriate HAPOI67 activity or levels.

DESCRIPTION OF THE INVENTION

Definitions

The following definitions are provided to facilitate understanding of certain terms used frequently herein. "HAPOI67" refers, among others, to a polypeptide comprising the amino acid sequence set forth in SEQ ID NO:2, or an allelic variant thereof.

"Receptor Activity" or "Biological Activity of the Receptor" refers to the metabolic or physiologic function of said HAPOI67 including similar activities or improved activities or these activities with decreased undesirable side-effects. Also included are antigenic and immunogenic activities of said HAPOI67.

"HAPOI67 gene" refers to a polynucleotide comprising the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to HAPOI67 polypeptides (or HAPOI67 proteins). The HAPOI67 polypeptides include the polypeptides of SEQ ID NOS:2 and 4; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within HAPOI67 polypeptides are polypeptides having the amino acid sequence which have at least 80% identity to the polypeptide having the amino acid sequence of SEQ ID NO: 2 over its entire length, and still more preferably at least 90% identity, and even still more preferably at least 95% identity to SEQ ID NO: 2. Furthermore, those with at least 97–99% are highly preferred. Preferably HAPOI67 polypeptides exhibit at least one biological activity of the receptor.

The HAPOI67 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the HAPOI67 polypeptides are also included in the invention. A fragment is a polypeptide having an amino acid sequence that entirely is the same as part, but not all, of the amino acid sequence of the aforementioned HAPOI67 polypeptides. As with HAPOI67 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of HAPOI67 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HAPOI67 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Among the most preferred fragment is that having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The HAPOI67 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to HAPOI67 polynucleotides. HAPOI67 polynucleotides include isolated polynucleotides which encode the HAPOI67 polypeptides and fragments, and polynucleotides closely related thereto. More specifically, the HAPOI67 polynucleotide of the invention includes a polynucleotide comprising the nucleotide sequence contained in SEQ ID NO:1 encoding a HAPOI67 polypeptide of SEQ ID NO: 2, and polynucleotides having the particular sequences of SEQ ID NOS:1 and 3. HAPOI67 polynucleotides further include a polynucleotide comprising a nucleotide sequence that has at least 80% identity over its entire length to a nucleotide sequence encoding the HAPOI67 polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under HAPOI67 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such HAPOI67 polynucleotides.

HAPOI67 of the invention is structurally related to other proteins of the G-protein coupled receptor family, as shown by the results of sequencing the cDNA encoding human HAPOI67. The cDNA sequence of SEQ ID NO:1 contains an open reading frame (nucleotide number 158 to 2113) encoding a polypeptide of 652 amino acids of SEQ ID NO:2. The amino acid sequence of Table 1 (SEQ ID NO:2) has about 41.0% identity (using FASTA) in 507 amino acid residues with Cell surface glycoprotein receptor (Accession # Q61549, Gordon, S. et al, J. Biol. Chem. 271: 486489, 1996). Furthermore, HAPOI67 (SEQ ID NO: 2) is 41.1% identical to Cell surface glycoprotein EMR1 over 514 amino acid residues (Accession # Q14246, Baud, V. et al, Genomics, 26: 334–344, 1995). The nucleotide sequence of Table 1 (SEQ ID NO:1) has about 95% identity (using BLAST) in 222 nucleotide residues with homo sapiens cDNA clone 213982 (Accession # H70763, Wilson, R. et al, WashU-Merck EST Project, unpublished, 1995). Furthermore, HAPOI67 (SEQ ID NO: 1) is 62.56% identical to human EMR1 hormone receptor over 804 nucleotide residues (Accession # X81479, Baud, V. et al, Genomics, 26 (2), 334–344, 1995). Thus, HAPOI67 polypeptides and polynucleotides of the present invention are expected to have, inter alia, similar biological functions/properties to their homologous polypeptides and polynucleotides, and their utility is obvious to anyone skilled in the art.

TABLE 1[a]

| | | | | |
|---|---|---|---|---|
| 1 | AAGCAGTTTG | CTTTTCTGAT | AGCAATTTCA | TGAGTCAGCT GACCTAAGAT |
| 51 | ACATACTTCA | ATTCTCATGG | GATTTCTTGA | GCTAGGAAAG GTGGTTGGCT |
| 101 | TACGGCACAG | TAGAGAGCTT | CCAGGGCTGG | CTGGCGTGGG ATACCCGTAC |
| 151 | CACAGAAATG | CAGGGACCAT | TGCTTCTTCC | AGGCCTCTGC TTTCTGCTGA |
| 201 | GCCTCTTTGG | AGCTGTGACT | CAGAAAACCA | AAACTTCCTG TGCTAAGTGC |
| 251 | CCCCCAAATG | CTTCCTGTGT | CAATAACACT | CACTGCACCT GCAACCATGG |
| 301 | ATATACTTCT | GGATCTGGGC | AGAAACTATT | CACATTCCCC TTGGAGACAT |
| 351 | GTAACGACAT | TAATGAATGT | ACACCACCCT | ATAGTGTATA TTGTGGATTT |
| 401 | AACGCTGTGT | GTTACAATGT | CGAAGGAAGT | TTCTACTGTC AATGTGTCCC |
| 451 | AGGATATAGA | CTGCATTCTG | GGAATGAACA | ATTCAGTAAT TCCAATGAGA |
| 501 | ACACCTGTCA | GGACACCACC | TCCTCAAAGA | CAACCCAGGG CAGGAAAGAG |
| 551 | CTGCAAAAGA | TTGTGGACAA | ATTTGAGTCA | CTTCTCACCA ATCAGACTTT |
| 601 | ATGGAGAACA | GAAGGGAGAC | AAGAAATCTC | ATCCACAGCT ACCACTATTC |
| 651 | TCCGGGATGT | GGAATCGAAA | GTTCTAGAAA | CTGCCTTGAA AGATCCAGAA |
| 701 | CAAAAAGTCC | TGAAAATCCA | AAACGATAGT | GTAGCTATTG AAACTCAAGC |

TABLE 1[a]-continued

```
 751 GATTACAGAC AATTGCTCTG AAGAAAGAAA GACATTCAAC TTGAACGTCC
 801 AAATGAACTC AATGGACATC CGTTGCAGTG ACATCATCCA GGGAGACACA
 851 CAAGGTCCCA GTGCCATTGC CTTTATCTCA TATTCTTCTC TTGGAAACAT
 901 CATAAATGCA ACTTTTTTTG AAGAGATGGA TAAGAAAGAT CAAGTGTATC
 951 TGAACTCTCA GGTTGTGAGT GCTGCTATTG ACCCAAAAG GAACGTGTCT
1001 CTCTCCAAGT CTGTGACGCT GACTTTCCAG CACGTGAAGA TGACCCCCAG
1051 TACCAAAAAG GTCTTCTGTG TCTACTGGAA GAGCACAGGG CAGGGCAGCC
1101 AGTGGTCCAG GGATGGCTGC TTCCTGATAC ACGTGAACAA GAGTCACACC
1151 ATGTGTAATT GCAGTCACCT GTCCAGCTTC GCTGTCCTGA TGGCCCTGAC
1201 CAGCCAGGAG GAGGATCCCG TGCTGACTGT CATCACCTAC GTGGGGCTGA
1251 GCGTCTCTCT GCTGTGCCTC CTCCTGGCGG CCCTCACTTT TCTCCTGTGT
1301 AAAGCCATCC AGAACACCAG CACCTCACTG CATCTGCAGC TCTCGCTCTG
1351 CCTCTTCCTG GCCCACCTCC TCTTCCTCGT GGGGATTGAT CGAACTGAAC
1401 CCAAGGTGCT GTGCTCCATC ATCGCCGGTG CTTTGCACTA TCTCTACCTG
1451 GCCGCCTTCA CCTGGATGCT GCTGGAGGGT GTGCACCTCT TCCTCACTGC
1501 ACGGAACCTG ACAGTGGTCA ACTACTCAAG CATCAATAGA CTCATGAAGT
1551 GGATCATGTT CCCAGTCGGC TATGGCGTTC CCGCTGTGAC TGTGGCCATT
1601 TCTGCAGCCT CCTGGCCTCA CCTTTATGGA ACTGCTGATC GATGCTGGCT
1651 CCACCTGGAC CAGGGATTCA TGTGGAGTTT CCTTGGCCCA GTCTGTGCCA
1701 TTTTCTCTGC GAATTTAGTA TTGTTTATCT TGGTCTTTTG GATTTTGAAA
1751 AGAAAACTTT CCTCCCTCAA TAGTGAAGTG TCAACCATCC AGAACACAAG
1801 GATGCTGGCT TTCAAAGCAA CAGCTCAGCT CTTCATCCTG GGCTGCACAT
1851 GGTGTCTGGG CTTGCTACAG GTGGGTCCAG CTGCCCAGGT CATGGCCTAC
1901 CTCTTCACCA TCATCAACAG CCTCCAAGGC TTCTTCATCT TCTTGGTCTA
1951 CTGCCTCCTC AGCCAGCAGG TCCAGAAACA ATATCAAAAG TGGTTTAGAG
2001 AGATCGTAAA ATCAAAATCT GAGTCTGAGA CATACACACT TTCCAGCAAG
2051 ATGGGTCCTG ACTCAAAACC CAGTGAGGGG GATGTTTTTC CAGGACAAGT
2101 GAAGAGAAAA TATTAAAACT AGAATATTCA ACTCCATATG GAAAATCATA
2151 TCCATGGATC TCTTTGGCAT TATGAAGAAT GAAGCTAAGG AAAAGGGAAT
2201 TCATTAAACA TATCATCCTT GGAGAGGAAG TAATCAACCT TTACTTCCCA
2251 AGCTGTTTGT TCTCCACAAT AGGCTCTCAA CAAATGTGTG GTAAATTGCA
2301 TTTCTCTTCA AAAAAAAAAA AAMAAAAA
```

[a]A nucleotide sequence of a human HAPOI67. SEQ ID NO: 1.

TABLE 2[b]

```
  1 MQGPLLLPGL CFLLSLFGAV TQKTKTSCAK CPPNASCVNN THCTCNHGYT
 51 SGSGQKLFTF PLETCNDINE CTPPYSVYCG FNAVCYNVEG SFYCQCVPGY
101 RLHSGNEQFS NSNENTCQDT TSSKTTQGRK ELQKIVDKFE SLLTNQTLWR
151 TEGRQEISST ATTILRDVES KVLETALKDP EQKVLKIQND SVAIETQAIT
```

TABLE 2^b-continued

```
201 DNCSEERKTF NLNVQMNSMD IRCSDIIQGD TQGPSAIAFI SYSSLGNIIN

251 ATFFEEMDKK DQVYLNSQVV SAAIGPKRNV SLSKSVTLTF QHVVMTPSTK

301 KVFCVYWKST GQGSQWSRDG CFLIHVNKSH TMCNCSHLSS FAVLMALTSQ

351 EEDPVLTVIT YVGLSVSLLC LLLAALTFLL CKAIQNTSTS LHLQLSLCLF

401 LAHLLFLVGI DRTEPKVLCS IIAGALHYLY LAAFTWMLLE GVHLFLTARN

451 LTVVNYSSIN RLMKWIMFPV GYGVPAVTVA ISAASWPHLY GTADRCWLHL

501 DQGFMWSFLG PVCAIFSANL VLFILVFWIL KRKLSSLNSE VSTIQNTRML

551 AFKATAQLFI LGCTWCLGLL QVGPAAQVMA YLFTIINSLQ GFFIFLVYCL

601 LSQQVQKQYQ KWFREIVKSK SESETYTLSS KMGPDSKPSE GDVFPGQVKR

651 KY*
```

^b An amino acid sequence of a human HAPOI67. SEQ ID NO: 2.

One polynucleotide of the present invention encoding HAPOI67 may be obtained using standard cloning and screening, from a cDNA library derived from mRNA in cells of the human spleen using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding the HAPOI67 polypeptide of SEQ ID NO:2 may be identical to the polypeptide encoding sequence contained in Table 1 (nucleotide number 158 to 2113 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of the HAPOI67 polypeptide, the polynucleotide may include the coding sequence for the mature polypeptide of a fragment thereof, by itself, the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding HAPOI67 variants comprising the amino acid sequence of the HAPOI67 polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO: 3) encoding the amino acid sequence f Table 4 (SEQ ID NO: 4).

TABLE 3^c

```
  1 GGCACGAGCT GGCGTGGGAT ACCCGTACCA CAGAAATGCA GGGACCATTG

51 CTTCTTCCAG GCCTCTGCTT TCTGCTGAGC CTCTTTGGAG CTGTGACTCA

101 GAAAACCAAA ACTTCCTGTG CTAAGTGCCC CCCAAATGCT TCCTGTGTCA

151 ATAACACTCA CTGCACCTGC AACCATGGAT ATACTTCTGG ATCTGGGCAG

201 AAACTATTCA CATTCCCCTT GGAGACATGT AACGACATTA ATGAATGTAC

251 ACCACCCTAT AGTGTATATT GTGGATTTAA CGCTGTGTGT TACAATGTCG

301 AAGGAAGTTT CTACTGTCAA TGTGTCCCAG GATATAGACT GCATTCTGGG

351 AATGAACAAT TCAGTAATTC CAATGAGAAC ACCTGTCAGG ACACCACCTC

401 CTCAAAGACA ACCCAGGGCA GGAAAGAGCT GCAAAAGATT GTGGACAAAT

451 TTGAGTCACT TCTCACCAAT CAGACTTTAT GGAGAACAGA AGGGAGACAA

501 GAAATCTCAT CCACAGCTAC CACTATTCTC CGGGATGTGG AATCGAAAGT

551 TCTAGAAACT GCCTTGAAAG ATCCAGAACA AAAAGTCCTG AAAATCCAAA
```

TABLE 3c-continued

```
 601 ACGATAGTGT AGCTATTGAA ACTCAAGCGA TTACAGACAA TTGCTCTGAA
 651 GAAAGAAAGA CATTCAACTT GAACGTCCAA ATGAACTCAA TGGACATCCG
 701 TTGCAGTGAC ATCATCCAGG GAGACACACA AGGTCCCAGT GCCATTGCCT
 751 TTATCTCATA TTCTTCTCTT GGAAACATCA TAAATGCAAC TTTTTTTGAA
 801 GAGATGGATA AGAAAGATCA AGTGTATCTG AACTCTCAGG TTGTGAGTGC
 851 TGCTATTGGA CCCAAAAGGA ACGTGTCTCT CTCCAAGTCT GTGACGCTGA
 901 CTTTCCAGCA CGTGAAGATG ACCCCCAGTA CCAAAAAGGT CTTCTGTGTC
 951 TACTGGAAGA GCACAGGGCA GGGCAGCCAG TGGTCCAGGG ATGGCTGCTT
1001 CCTGATACAC GTGAACAAGA GTCACACCAT GTGTAATTGC AGTCACCTGT
1051 CCAGCTTCGC TGTCCTGATG GCCCTGACCA GCCAGGAGGA GGATCCCGTG
1101 CTGACTGTCA TCACCTACGT GGGGCTGAGC GTCTCTCTGC TGTGCCTCCT
1151 CCTGGCGGCC CTCACTTTTC TCCTGTGTAA AGCCATCCAG AACACCAGCA
1201 CCTCACTGCA TCTGCAGCTC TCGCTCTGCC TCTTCCTGGC CCACCTCCTC
1251 TTCCTCGTGG GGATTGATCG AACTGAACCC AAGGTGCTGT GCTCCATCAT
1301 CGCCGGTGCT TTGCACTATC TCTACCTGGC CGCCTTCACC TGGATGCTGC
1351 TGGAGGGTGT GCACCTCTTC CTCACTGCAC GGAACCTGAC AGTGGTCAAC
1401 TACTCAAGCA TCAATAGACT CATGAAGTGG ATCATGTTCC CAGTCGGCTA
1451 TGGCGTTCCC GCTGTGACTG TGGCCATTTC TGCAGCCTCC TGGCCTCACC
1501 TTTATGGAAC TGCTGATCGA TGCTGGCTCC ACCTGGACCA GGGATTCATG
1551 TGGAGTTTCC TTGGCCCAGT CTGTGCCATT TTCTCTGCGA ATTTAGTATT
1601 GTTTATCTTG GTCTTTTGGA TTTTGAAAAG AAAACTTTCC TCCCTCAATA
1651 GTGAAGTGTC AACCATCCAG AACACAAGGA TGCTGGCTTT CAAAGCAACA
1701 GCTCAGCTCT TCATCCTGGG CTGCACATGG TGTCTGGGCT GCTACAGGT
1751 GGGTCCAGCT GCCCAGGTCA TGGCCTACCT CTTCACCATC ATCAACAGCC
1801 TCCAAGGCTT CTTCATCTTC TTGGTCTACT GCCTCCTCAG CCAGCAGGTC
1851 CAGAAACAAT ATCAAAAGTG GTTTAGAGAG ATCGTAAAAT CAAAATCTGA
1901 GTCTGAGACA TACACACTTT CCAGCAAGAT GGGTCCTGAC TCAAAACCCA
1951 GTGAGGGGGA TGTTTTTCCA GGACAAGTGA AGAGAAAATA TTAAAACTAG
2001 AATATTCAAC TCCATATGGA AAATCATATC CATGGATCTC TTTGGCATTA
2051 TGAAGAATGA AGCTAAGGAA AAGGGAATTC ATTAAACATA TCATCCTTGG
2101 AGAGGAAGTA ATCAACCTTT ACTTCCCAAG CTGTTTGTTC TCCACAATAG
2151 GCTCTCAACA AATGTGTGGT AAATTGCATT TCTCTTCAAA AAAAAAAAA
2201 AAAAAA
``` cA partial nucleotide sequence of a human HAPOI67. SEQ ID NO: 3.

TABLE 4d

```
  1 LQKIVDKFES LLTNQTLWRT EGRQEISSTA TTILRDVESK VLETALKDPE
 51 QKVLKIQNDS VAIETQAITD NCSEERKTFN LNVQMNSMDI RCSDIIQGDT
101 QGPSAIAFIS YSSLGNIINA TFFEEMDKKD QVYLNSQVVS AAIGPKRNVS
```

TABLE 4[d]-continued

```
151 LSKSVTLTFQ HVKMTPSTKK VFCVYWKSTG QGSQWSRDGC FLIHVNKSHT

201 MCNCSHLSSF AVLMALTSQE EDPVLTVITY VGLSVSLLCL LLAALTFLLC

251 KAIQNTSTSL HLQLSLCLFL AHLLFLVGID RTEPKVLCSI IAGALHYLYL

301 AAFTWMLLEG VHLFLTARNL TVVNYSSINR LMKWIMFPVG YGVPAVTVAI

351 SAASWPHLYG TADRCWLHLD QGFMWSFLGP VCAIFSANLV LFILVFWILK

401 RKLSSLNSEV STIQNTRMLA FKATAQLFIL GCTWCLGLLQ VGFAAQVMAY

451 LFTIINSLQG FFIFLVYCLL SQQVQKQYQK WFREIVKSKS ESETYTLSSK

501 MGFDSKFSEG DVFFGQVKRK Y*
```

[d]A partial amino acid sequence of a human HAPOI67. SEQ ID NO: 4.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof, may be used as hybridization probes for cDNA and genomic DNA, to isolate full-length cDNAs and genomic clones encoding HAPOI67 and to isolate cDNA and genomic clones of other genes (including genes encoding homologs and orthologs from species other than human) that have a high sequence similarity to the HAPOI67 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

One embodiment, to obtain a polynucleotide encoding the HAPOI67 polypeptide, including homologs and orthologs from species other than human, comprises the steps of screening an appropriate library under stingent hybridization conditions with a labeled probe having the SEQ ID NO: 1 or a fragment thereof (including that of SEQ ID NO: 3), and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli,* Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HAPOI67 polypeptide is to be expressed for use in screening assays, generally, it is preferred that the polypeptide be produced at the surface of the cell. In this event, the cells may be harvested prior to use in the screening assay. If the HAPOI67 polypeptide is secreted into the medium, the medium can be recovered in order to recover and purify the polypeptide; if produced intracellularly, the cells must first be lysed before the polypeptide is recovered.

HAPOI67 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HAPOI67 polynucleotides for use as diagnostic reagents. Detection of a mutated form of the HAPOI67 gene associated with a dysfunction will provide a diagnostic tool that can add to or define a diagnosis of a disease or susceptibility to a disease which results from under-expression, over-expression or altered expression of HAPOI67. Individuals carrying mutations in the HAPOI67 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HAPOI67 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985)230:1242. Sequence changes at specific locations may also be revealed by nuclease protection assays, such as RNase and S1 protection or the chemical cleavage method. See Cotton et al., *Proc Natl Acad Sci USA* (1985) 85: 4397–4401. In another embodiment, an array of oligonucleotide probes comprising the HAPOI67 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome through detection of mutation in the HAPOI67 gene by the methods described.

In addition, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, can be diagnosed by methods comprising determining from a sample derived from a subject an abnormally decreased or increased level of the HAPOI67 polypeptide or HAPOI67 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HAPOI67, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, which comprises:

(a) an HAPOI67 polynucleotide, preferably the nucleotide sequence of SEQ ID NO: 1, or a fragment thereof;

(b) a nucleotide sequence complementary to that of (a);

(c) an HAPOI67 polypeptide, preferably the polypeptide of SEQ ID NO: 2, or a fragment thereof, or (d) an antibody to an HAPOI67 polypeptide, preferably to the polypeptide of SEQ ID NO: 2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them an also be used as immunogens to produce antibodies immunospecific for the HAPOI67 polypeptides. The term "immunospecific" means that the antibodies have substantiall greater affinity for the polypeptides of the invention than their affinity for other related polypeptides in the prior art.

Antibodies generated against the HAPOI67 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HAPOI67 polypeptides may also be employed to treat infections such as bacterial, fungal, protozoan and viral infections, particularly infections caused by HV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

Vaccines

Another aspect of the invention relates to a method for inducing an immunological response in a mammal which comprises inoculating the mammal with the HAPOI67 polypeptide, or a fragment thereof, adequate to produce antibody and/or T cell immune response to protect said animal from infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. Yet another aspect of the invention relates to a method of inducing immunological response in a mammal which comprises delivering the HAPOI67 polypeptide via a vector directing expression of the HAPOI67 polynucleotide in vivo in order to induce such an immunological response to produce antibody to protect said animal from diseases.

A further aspect of the invention relates to an immunological/vaccine formulation (composition) which, when introduced into a mammalian host, induces an immunological response in that mammal to an HAPOI67 polypeptide wherein the composition comprises an HAPOI67 polypeptide or HAPOI67 gene. The vaccine formulation may further comprise a suitable carrier. Since the HAPOI67 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The HAPOI67 polypeptide of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al, Current Protocols in Immunology 1(2):Chapter 5 (1991).

HAPOI67 polypeptides are responsible for many biological functions, including many pathologies. Accordingly, it is desirous to find compounds and drugs which stimulate HAPOI67 on the one hand and which can inhibit the function of HAPOI67 on the other hand. In general, agonists are employed for therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome. Antagonists may be employed for a variety of therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

In general, such screening procedures involve producing appropriate cells which express the receptor polypeptide of the present invention on the surface thereof. Such cells include cells from mammals, yeast, Drosophila or *E. coli*. Cells expressing the receptor (or cell membrane containing the expressed receptor) are then contacted with a test compound to observe binding, or stimulation or inhibition of a functional response.

One screening technique includes the use of cells which express the receptor of this invention (for example, transfected CHO cells) in a system which measures extracellular pH or intracellular calcium changes caused by receptor activation. In this technique, compounds may be contacted with cells expressing the receptor polypeptide of the present invention. A second messenger response, e.g., signal transduction, pH changes, or changes in calcium level, is then measured to determine whether the potential compound activates or inhibits the receptor.

Another method involves screening for receptor inhibitors by determining inhibition or stimulation of receptor-mediated cAMP and/or adenylate cyclase accumulation. Such a method involves transfecting a eukaryotic cell with the receptor of this invention to express the receptor on the cell surface. The cell is then exposed to potential antagonists in the presence of the receptor of this invention. The amount of cAMP accumulation is then measured. If the potential antagonist binds the receptor, and thus inhibits receptor binding, the levels of receptor-mediated cAMP, or adenylate cyclase, activity will be reduced or increased.

Another method for detecting agonists or antagonists for the receptor of the present invention is the yeast based technology as described in U.S. Pat. No. 5,482,835, incorporated by reference herein.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed.

Further, the assays may simply comprise the steps of mixing a candidate compound with a solution containing an HAPOI67 polypeptide to form a mixture, measuring the HAPOI67 activity in the mixture, and comparing the HAPOI67 activity of the mixture to a standard.

The HAPOI67 cDNA, protein and antibodies to the protein may also be used to configure assays for detecting the effect of added compounds on the production of HAPOI67 mRNA and protein in cells. For example, an ELISA may be constructed for measuring secreted or cell associated levels of HAPOI67 protein using monoclonal and polyclonal antibodies by standard methods known in the art, and this can be used to discover agents which may inhibit or enhance the production of HAPOI67 (also called antagonist or agonist, respectively) from suitably manipulated cells or tissues. Standard methods for conducting screening assays are well understood in the art.

Examples of potential HAPOI67 antagonists include antibodies or, in some cases, oligonucleotides or proteins which are closely related to the ligand of the HAPOI67, e.g., a fragment of the ligand, or small molecules which bind to the receptor but do not elicit a response, so that the activity of the receptor is prevented.

Thus in another aspect, the present invention relates to a screening kit for identifying agonists, antagonists, ligands, receptors, substrates, enzymes, etc. for HAPOI67 polypeptides; or compounds which decrease or enhance the production of HAPOI67 polypeptides, which comprises:

(a) an HAPOI67 polypeptide, preferably that of SEQ ID NO:2;

(b) a recombinant cell expressing an HAPOI67 polypeptide, preferably that of SEQ ID NO:2;

(c) a cell membrane expressing an HAPOI67 polypeptide; preferably that of SEQ ID NO: 2; or (d) antibody to an HAPOI67 polypeptide, preferably that of SEQ ID NO: 2.

It will be appreciated that in any such kit, (a), (b), (c) or (d) may comprise a substantial component.

Prophylactic and Therapeutic Methods

This invention provides methods of treating an abnormal conditions related to both an excess of and insufficient amounts of HAPOI67 activity.

If the activity of HAPOI67 is in excess, several approaches are available. One approach comprises administering to a subject an inhibitor compound (antagonist) as hereinabove described along with a pharmaceutically acceptable carrier in an amount effective to inhibit activation by blocking binding of ligands to the HAPOI67, or by inhibiting a second signal, and thereby alleviating the abnormal condition.

In another approach, soluble forms of HAPOI67 polypeptides still capable of binding the ligand in competition with endogenous HAPOI67 may be administered. Typical embodiments of such competitors comprise fragments of the HAPOI67 polypeptide.

In still another approach, expression of the gene encoding endogenous HAPOI67 can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of HAPOI67 and its activity, several approaches are also available. One approach comprises administering to a subject a therapeutically effective amount of a compound which activates HAPOI67, i.e., an agonist as described above, in combination with a pharmaceutically acceptable carrier, to thereby alleviate the abnormal condition. Alternatively, gene therapy may be employed to effect the endogenous production of HAPOI67 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and Other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of HAPOI67 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLE 1
Mammalian Cell Expression

The receptors of the present invention are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G418-resistant clones analyzed.

EXAMPLE 2
Ligand Bank for Binding and Functional Assays.

A bank of over 200 putative receptor ligands has been assembled for screening. The bank comprises: transmitters, hormones and chemokines known to act via a human seven transmembrane (7TM) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc, (see below)) as well as binding assays.

EXAMPLE 3
Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

EXAMPLE 4
Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

EXAMPLE 5
Microphysiometric Assays

Activation of a wide variety of secondary messenger systems results in extrusion of small amounts of acid from a cell. The acid formed is largely a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

EXAMPLE 6
Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequentially subfractionated until an activating ligand is isolated and identified.

EXAMPLE 7
Calcium and cAMP Functional Assays

7TM receptors which are expressed in HEK 293 cells have been shown to be coupled functionally to activation of PLC and calcium mobilization and/or cAMP stimuation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day greater than 150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP flucuation are tested in vector control cells to determine if the response is unique to the transfected cells expressing receptor.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising the nucleotide sequence of SEQ ID NO:1.

2. The isolated polynucleotide of claim 1 comprising an RNA sequence corresponding to the entire length of the nucleotide sequence set forth in SEQ ID NO:1.

3. An isolated polynucleotide comprising nucleotides 158 to 2113 of SEQ ID NO:1.

4. An isolated polynucleotide comprising an RNA sequence corresponding to nucleotides 158 to 2113 of the nucleotide sequence set forth in SEQ ID NO:1.

5. An isolated polynucleotide comprising a nucleotide sequence fully complementary to the sequence set forth in SEQ ID NO:1.

* * * * *